United States Patent [19]

Gewartowski

[11] 4,343,958
[45] * Aug. 10, 1982

[54] HYDROCARBON ISOMERIZATION PROCESS

[75] Inventor: Steve A. Gewartowski, Mt. Prospect, Ill.

[73] Assignee: UOP Inc., Des Plaines, Ill.

[*] Notice: The portion of the term of this patent subsequent to Feb. 26, 1997, has been disclaimed.

[21] Appl. No.: 258,334

[22] Filed: Apr. 28, 1981

Related U.S. Application Data

[63] Continuation-in-part of Ser. No. 78,403, Sep. 24, 1979, abandoned, which is a continuation-in-part of Ser. No. 866,663, Jan. 3, 1978, Pat. No. 4,190,520.

[51] Int. Cl.$^3$ .......................... C07C 5/22; C07C 5/13
[52] U.S. Cl. ................................... 585/477; 208/95; 208/100; 208/134; 585/734
[58] Field of Search ............... 196/134; 208/95, 100; 585/477, 734

[56] References Cited

U.S. PATENT DOCUMENTS

| | | | |
|---|---|---|---|
| 2,284,493 | 5/1942 | Noll et al. | 208/78 |
| 2,666,022 | 1/1954 | Johnson | 208/46 |
| 3,283,021 | 11/1966 | Hardison | 260/666 |
| 3,529,030 | 9/1970 | Chin | 585/477 |
| 3,755,144 | 8/1973 | Asselin | 208/95 |
| 3,873,440 | 3/1975 | Hallman | 208/108 |
| 4,190,520 | 2/1980 | Gewartowski | 208/95 |

FOREIGN PATENT DOCUMENTS 1289850  2/1962  France .

OTHER PUBLICATIONS

Hydrocarbon Processing, Sep. 1978, p. 170, "C$_5$/C$_6$ Isomerization".
Hydrocarbon Processing, Nov. 1973, p. 197, "Xylene Isomerization (Isomar)".

*Primary Examiner*—Curtis R. Davis
*Attorney, Agent, or Firm*—James R. Hoatson, Jr.; John F. Spears, Jr.; William H. Page, II

[57] ABSTRACT

A process for the isomerization of acyclic hydrocarbons and alkylaromatic hydrocarbons is disclosed. The mixed-phase feed stream is heated and the liquid-phase portion of the feed stream is simultaneously vaporized by indirect heat exchange against the effluent of the reaction zone. Prior to this exchange, the effluent of the isomerization zone is heated in a fired heater to a temperature above that employed in the reaction zone. The inventive concept eliminates the need to pass mixed-phase feed streams through fired multi-pass heaters.

7 Claims, 1 Drawing Figure

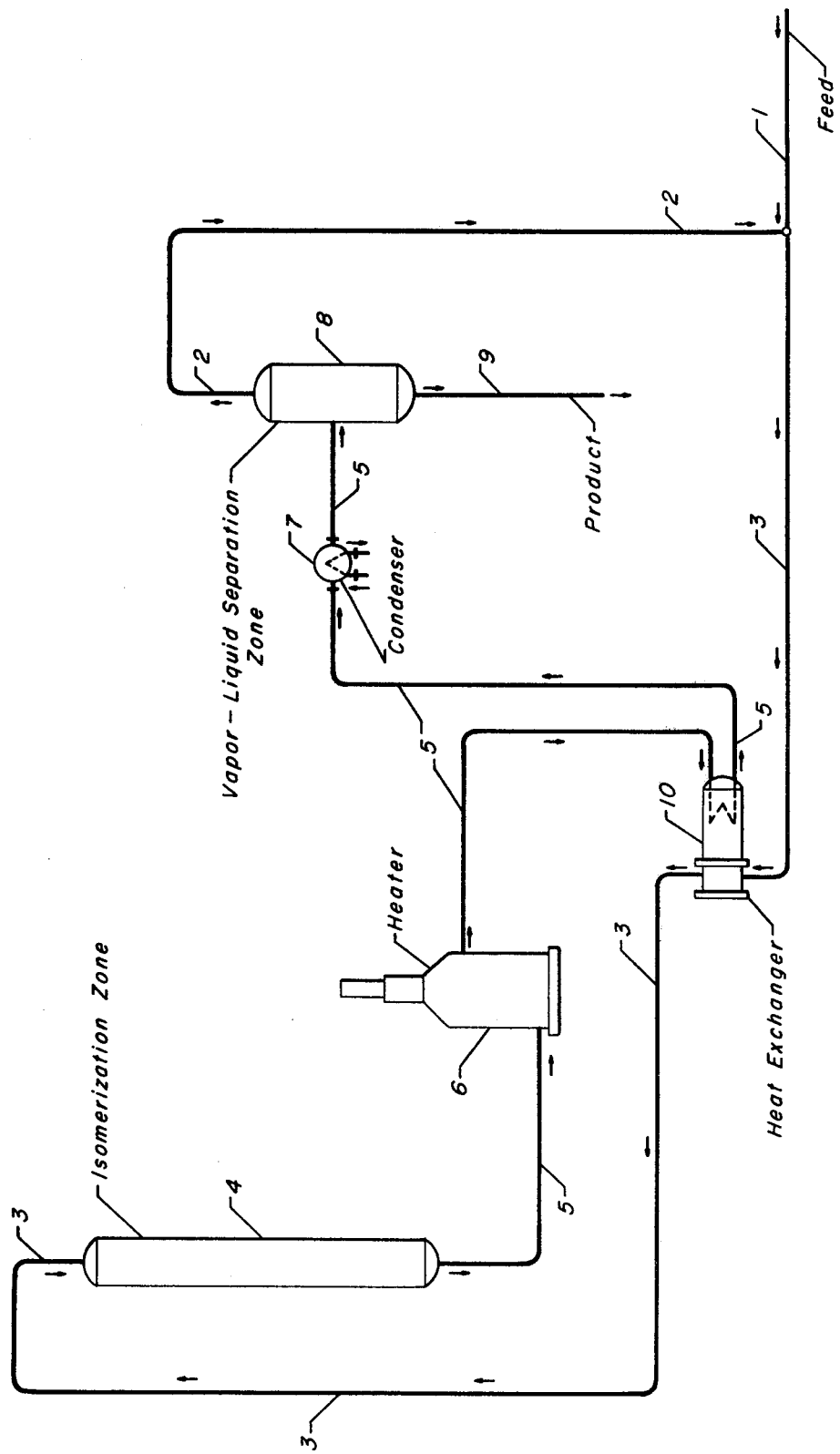

HYDROCARBON ISOMERIZATION PROCESS

CROSS-REFERENCE TO RELATED APPLICATIONS

This application is a continuation-in-part of my prior copending application Ser. No. 78,403 filed Sept. 24, 1979, and now abandoned which was a continuation-in-part of my then copending application Ser. No. 866,663 filed on Jan. 3, 1978 and now U.S. Pat. No. 4,190,520. The teachings of my prior applications are incorporated herein by reference.

FIELD OF THE INVENTION

The invention relates to a hydrocarbon conversion process. The invention more specifically relates to a process for the isomerization of acyclic $C_5$-plus hydrocarbons and to a process for the isomerization of alkylaromatic hydrocarbons. The invention also relates to the use of indirect heat exchange to recover heat from the effluent stream of a reaction zone. The inventive concept may be applied to many processes described in U.S. patents classified in Classes 208 and 585.

PRIOR ART

The isomerization of hydrocarbons is a well developed and widely practiced process in the petrochemical and petroleum refining industries. The standard process flow in these processes is to heat the feed stream first by indirect heat exchange against the effluent of the isomerization zone and then by passage through a fired heater or a similar available source of high temperature heat. For the isomerization of acyclic hydrocarbons, this is shown in U.S. Pat. Nos. 3,283,021 (Cl. 260-666) and 3,755,144 (Cl. 208-95) and at page 170 of the Sept., 1978 edition of *Hydrocarbon Processing*. For the isomerization of alkylaromatic hydrocarbons, such as xylenes, this is shown at page 197 of the Nov., 1973 edition of *Hydrocarbon Processing*. It is believed that the heating of the effluent of the isomerization zone followed by heat exchange against the feed stream has not been practiced.

Some steps used in the subject process are performed in the prior art. These include the heat exchange of the feed stream to the isomerization zone with the effluent of the isomerization zone to recover heat from the effluent stream. The partial condensation of the effluent stream followed by its separation in a phase separation zone into a liquid product stream and a recycle hydrogen stream is also well known.

In the subject process, the effluent stream of the isomerization zone is first heated in a fired heater and is then heat exchanged against the feed stream. That is, the heater required to sufficiently heat the feed stream is located downstream of the reaction zone. The subject process is therefore readily distinguished from a process such as that described in U.S. Pat. No. 2,284,493 wherein a stream which is derived only in part from the effluent of a reaction zone is heated in a second reaction zone and is then heat exchanged against the feed stream to the process. The heat exchange shown in this reference is designed to optimize heat recovery and to utilize available high temperature process streams as heat sources. It is also believed the visbreaking and thermal reforming process of this reference does not have the problems of mixed-phase flow which the subject process addresses.

French Pat. No. 1,289,850 is pertinent to the subject invention for its description of a process flow suitable for a catalytic hydrogenation process. In this process the feed stream to the reaction zone is heated by indirect heat exchange against all or a portion of the reaction zone effluent stream after the reaction zone effluent stream has been heated. This reference also discloses that if the reaction zone effluent stream is a mixed-phase stream then only one of the two phases may be heated and used for heating the feed stream. However, this reference appears to be directed only to overcoming the problem of heating very temperature-sensitive hydrocarbons, such as pyrolysis gasolines which contain diolefins, and to be limited in its teaching to the hydrogenation of such materials. It is believed that the reference does not suggest an appreciation of the inventive concept claimed herein which is directed to the broader problem of heating mixed-phase process streams. As evidence of this it is noted that in the example of the reference a mixed-phase effluent of the reaction zone is heated, whereas according to the subject inventive concept, only a single vapor-phase is ever heated by a high temperature heat source such as a furnace. It is also believed that the reference does not disclose a process in which the liquid phase portion of a feed stream is vaporized by heat exchange against a heated product stream or suggest the use of such a step in an isomerization process.

BRIEF SUMMARY OF THE INVENTIVE CONCEPT

The invention provides a hydrocarbon isomerization process which eliminates the problems associated with heating a mixed-phase feed stream in a fired heater. In the subject process the feed stream is brought up to the required reaction zone inlet temperature by heat exchange against the vapor-phase reactor effluent instead of by passage through a heater. Potential damage to the tubes used to heat the feed stream is thereby greatly reduced. This is because the maximum temperature difference between the inner and outer surface of the tubes is much less in such a feed-effluent heat exchanger than in a fired heater in which the tubes are directly exposed to combustion zone conditions.

One broad embodiment of the invention may be characterized as a hydrocarbon isomerization process which comprises the steps of vaporizing the liquid-phase portion of a mixed-phase isomerization zone feed stream which comprises a $C_5$-$C_{12}$ hydrocarbon and also heating the isomerization zone feed stream to an isomerization temperature by indirect heat exchange against a vapor-phase process stream; passing the isomerization zone feed stream through a hydrocarbon isomerization zone containing an isomerization catalyst and maintained at isomerization conditions and thereby forming a vapor-phase isomerization zone effluent stream which comprises two different hydrocarbons; heating at least a portion of the isomerization zone effluent stream in a fired heater; and cooling the heated portion of the isomerization zone effluent stream by indirect heat exchange against the feed stream as the previously referred to vapor-phase process stream.

DESCRIPTION OF THE DRAWING

The drawing illustrates one embodiment of the invention in which it is applied to a process for the isomerization of $C_6$ acyclic hydrocarbons. For simplicity and clarity, a number of pieces of apparatus normally required in the operation of the process have not been shown. This deleted apparatus includes pressure, flow and temperature control systems, vessel internals, etc., all of which may be of customary design. This depiction of one embodiment of the invention is not intended to exclude from the inventive concept those other embodiments set out herein or which are the result of normal and reasonable modification of those embodiments.

Referring now to the drawing, a feed stream which is rich in a $C_6$ acyclic hydrocarbon enters the process through line 1. The feed stream is admixed with a recycle gas stream carried by line 2 and passed through an indirect heat exchange means 10 via line 3. The liquid present in the feed stream is vaporized in this heat exchange means and the feed stream is also heated to the desired inlet temperature of the isomerization zone 4. The feed stream is then passed into the isomerization zone and contacted with a bed of isomerization catalyst maintained at isomerization-promoting conditions.

The vapor-phase effluent stream of the isomerization zone is removed in line 5 and passed through a fired heater 6 wherein it is heated to a temperature above that employed in the isomerization zone. The effluent stream of the isomerization zone is then cooled by heat exchange against the feed stream in heat exchange means 10. The effluent stream is partially condensed in the condenser 7 and passed into a vapor-liquid separation zone 8. The liquid-phase portion of the isomerization zone effluent stream is removed from the process through line 9 as a product stream which may be consumed directly or passed into a product recovery or fractionation zone. The uncondensed portion of the isomerization zone effluent stream is withdrawn from the separation zone as the hydrogen-rich recycle gas stream carried by line 2.

DETAILED DESCRIPTION

In a great many processes used in the petroleum, chemical and petrochemical industries, it is necessary to heat a process feed stream prior to passing the feed stream into a reaction zone. Often this feed stream is a mixed-phase stream having both vapor phase and liquid phase components. Another frequent occurrence is that the furnaces or heaters used to raise these feed streams to the proper inlet temperatures must be multi-pass heaters. The various problems associated with heating mixed-phase streams in multi-pass fired heaters therefore arise frequently.

One of the largest problems in heaters used in this particular service is the maldistribution of the vapor and liquid phases within the heater tubes. The result of this maldistribution may be very uneven temperature profiles between or within heater tubes and the creation of localized areas of excessive temperature. For instance, a large body of liquid which accumulates at a low point in a tube may block vapor flow through one or more tubes of the heater, thus disrupting the normal two phase flow and possibly resulting in periods of little or no flow in the tubes so affected. The normal flow of these fluids through the heater tubes removes heat from the wall of the tubes and therefore serves to limit the maximum temperature reached by the tubes. A diminished or interrupted fluid flow decreases the rate of heat removal from the tubes by decreasing heat transfer to the fluids. This allows the tubes to reach higher temperatures which may cause coke deposits to form or may cause undesired thermocracking of the fluids. Long term maldistribution of the liquid flow may result in the tubes being weakened by excessive operating temperatures. This can lead to the rupture of the heater tubes, and may cause the catastrophic leakage of the highly flammable feed stream into the heater.

It is therefore an objective of the invention to provide a hydrocarbon conversion process wherein the problems associated with the maldistribution of mixed-phase feed streams in fired heaters are reduced. It is another objective of the invention to improve the operation of processes utilizing multi-pass fired heaters. A further objective of the invention is to provide a process for the isomerization of hydrocarbons, including the isomerization of $C_4$–$C_{12}$ paraffins and $C_7$–$C_9$ aromatic hydrocarbons.

The subject invention utilizes both a heater, preferably a fired heater, and an indirect heat exchange means. Both of these pieces of apparatus may be designed and built according to customary standards and methods which correspond to the conditions of temperature and pressure attributable to use in the process of the invention. As used herein, the term "multi-pass heater" is intended to refer to a heater which has piping arranged to allow entering fluid to divide between several alternative flow paths through the high temperature radiant heating area of the heater. The term "fired heater" is used to indicate an open flame is maintained within a heater. The invention is used in conjunction with a reactor or reaction zone. A fixed, moving, ebulliated or fluidized bed reactor may be used within the reaction zone. The reaction zone may contain two or more reactors in series or in a parallel flow arrangement. The design and operation of the reaction zone may be the same as is customary for the specific conversion process being performed.

In the method of the invention the feed stream is brought up to the desired inlet temperature of the reaction zone in an indirect heat exchange zone. Since the fluid quantities involved are quite large, the surface area needed in the heat exchange zone may require the use of several banks of individual heat exchangers. The use of countercurrent flow in shell and tube exchangers is preferred, but other types of exchangers may be substituted. Besides being heated in the indirect heat exchange zone all, or a portion, of any liquid-phase hydrocarbons in the feed stream are vaporized. Vaporization of the total feed stream prior to the reaction step is normally required in isomerization processes.

After being heated in the indirect head exchange zone, the feed stream is passed through the reaction zone. Various gas, recycle and additive streams can be admixed with the feed stream between the heat exchange zone and the reaction zone, but they are preferably added upstream of the heat exchange zone. A wide variety of isomerization reactions may be performed in the reaction zone. The specific reaction is preferably exothermic but may be endothermic. It is therefore preferred that the reaction zone effluent stream has a higher temperature and enthalpy than the reaction zone feed stream does as it enters the reaction zone.

Preferably all of the reaction zone effluent stream is in the vapor-phase and is passed directly into a fired heater. However, if the reaction zone effluent stream is a mixed-phase stream, it is preferably passed into a vapor-liquid separation zone. The vapor and the liquid phase portions of the reaction zone effluent stream are then separated into individual streams. Both or only one of these streams may be passed through the heating zone. If both streams are heated, they are at all times kept separate while in the heating zone. Two-phase flow through the heater is then totally avoided. Preferably, only the liquid phase portion of the effluent stream is heated if it is present in a sufficient quantity. The heated portion of the reaction zone effluent stream is then passed through the indirect heat exchange zone to effect the heating of the feed stream.

In order to heat the feed stream to the desired inlet temperature of the reaction zone, it is necessary that the heated portion of the reaction zone effluent stream which is passed into the indirect heat exchange zone has a temperature above the desired inlet temperature of the reaction zone. The exact temperature required will depend on such factors as the flow rates of the two streams fed to the indirect heat exchange zone and the surface area available within this zone. The maximum possible amount of heated reaction zone effluent is equal to the flow rate of the feed stream, and a temperature difference or approach of at least 15-20 Fahrenheit degrees is normally required in an indirect heat exchanger. Therefore, the heated portion of the reaction zone effluent which is passed into the indirect heat exchange zone should, as a minimum, have a temperature 15-20 Fahrenheit degrees above the desired inlet temperature of the reaction zone.

The subject operating method has several advantages, all which may not be present in any one particular application. For instance, in some processes the reactor effluent may cause less fouling of the heater tubes than the feed stream even at the higher temperature utilized in the subject process. Secondly, if the effluent of the reaction zone is a vapor phase stream there is no possibility of liquid maldistribution in the heater. A third advantage is present when a mixed-phase reaction zone effluent stream is produced in a process having a recycle gas stream. In this situation, the pressure drop across the heater is out of the recycle gas circuit. This reduces the utilities cost of operating the process.

Recycle gas streams are used in most processes including those for the isomerization of acyclic and alkylaromatic hydrocarbons. These recycle gas streams will often be rich in hydrogen and preferably contain 80-90 mole percent or more hydrogen. Hydrogen may be passed through the reaction zone for several reasons. These include aiding the vaporization of the reactants, the maintenance of catalyst activity and the prevention of excessive coke deposition. In some processes, the desired purity of the recycle stream may be maintained rather easily, as by the use of a drag stream or by the judicious control of the amount of light material which is removed in various liquid streams including condensates. This is normally true of the typical isomerization processes. The recycle gas may be purified by partial condensation or by absorption operations and enriched by the addition of makeup hydrogen. Unless otherwise specified, as used herein, any reference to a stream as being "rich" in a particular compound is intended to indicate that the concentration of that compound in the stream is above 60 mole percent.

The operation of the heater, or more specifically the rate at which fuel is supplied to the heater, may be controlled by one or more temperature measurements taken at the inlet of the reaction zone or within the reaction zone. Temperature measurements used in the heater control system may also be taken as the feed stream exits the indirect heat exchange zone. The operation of the heater will be adjusted as required to provide the temperature required within the reaction zone for the desired degree of conversion. This temperature will vary as the catalyst ages. Other variables which may require adjustment of the rate of flow of fuel to the heater include the rate of flow of the feed stream and its initial temperature prior to entering the indirect heat exchange zone.

The effluent of the reaction zone is not cooled prior to passage into the heater or into a vapor-liquid separation zone located upstream of the heater. If a vapor-liquid separation zone is used, it may be designed and constructed in a customary manner. A great many designs for vapor-liquid separators exist. Representative examples are the apparatus shown in U.S. Pat. Nos. 3,364,657; 3,826,064; 3,853,513; 3,873,283 and 3,900,000. In many instances, a relatively simple knockout drum with a demisting blanket will be sufficient. Guidelines on the design of knockout drums are contained in the article at page 155 of the June, 1961 edition of *Hydrocarbon Processing and Petroleum Refiner*.

In the preferred embodiment of the invention a $C_7$-$C_9$ aromatic hydrocarbon is isomerized in the reaction zone under vapor phase conditions as described in U.S. Pat. Nos. 2,784,241; 2,976,332; 3,078,318; 3,281,482; 3,304,339; 3,553,276 and 3,996,305. These references describe both catalysts and process conditions. An example of such a process is the isomerization of a mixture of xylene isomers in order to reestablish an equilibrium mixture of the isomers. This is performed commercially in combination with separatory processes which remove one or more of the isomers from a mixture of the isomers, with the remaining components of the equilibrium mixture being recycled to the isomerization process.

In the preferred embodiment the reaction zone is operated at conditions effective to cause the isomerization of aromatic hydrocarbons. Besides the presence of a catalyst, these conditions include a temperature of about 0° C. to about 600° C., preferably 320° C. to about 450° C., and a pressure of from about 1.0 to 100 atmospheres. Preferred is a pressure in the range of about 7 to 28 atmospheres and the use of a single fixed bed reactor operated with a downward flow of vapor phase reactants. The rate of hydrogen circulation should be sufficient to maintain a hydrogen to hydrocarbon mole ratio of from 1:1 to 20:1 in the reactor. This ratio is preferably kept within the range of about 1.5:1 to about 5:1. The amount of catalyst loaded in the reactor should provide a weight hourly space velocity (weight of hydrocarbons passing through the reactor in one hour per unit weight of catalyst) of about 0.05 to about 10 and preferably about 1 to 5. The exact conditions employed will normally vary with the age of the catalyst and are set by the activity of the catalyst and the effect of the conditions on selectivity, conversion and ultimate yield of the isomerization zone.

Central to operation of the aromatic hydrocarbon isomerization zone is an effective isomerization catalyst. Several different suitable formulations are known to those skilled in the art and effective catalysts are available commercially. The catalyst will typically comprise an acidic inorganic oxide support such as alumina, silica-alumina mixtures, faujasites and mordenites which have been combined or impregnated with a metallic component. Preferred is an alumina based catalyst containing about 0.05 to about 5.0 wt. % of a Group VIII metallic component and 0.3 to 5.0 wt. % halogen. Particularly preferred is about 0.1 to about 1.5 wt. % of platinum or palladium and about 0.5 to 2.5 wt. % fluorine or about 0.1 to 1.5 wt. % chlorine. This halogen concentration may be maintained by the injection of halogen-containing substances such as carbontetrachloride into the material entering the isomerization zone. These catalytic composites may also contain from about 0.1 to about 1.0 wt. % sulfur to improve their performance. All percentages given in reference to catalyst composition are calculated on an elemental basis. Other catalysts which may be employed in the isomerization zone are described in some detail in U.S. Pat. Nos. 3,464,929; 3,409,685 and 3,409,686. The catalysts described in these references include an alumina matrix having less than 20 wt. % of finely divided mordenite dispersed in it and containing at least one metallic component chosen from nickel, platinum and palladium, about 0.001 to 2.0 wt. % sulfur and about 0.2 to 3.0 wt. % chlorine or fluorine. A second catalyst disclosed in these references has a base comprising an alumina matrix with less than 20 wt. % of finely divided mordenite dispersed in it and contains about 0.05 to 5.0 wt. % platinum, or preferably palladium, and about 0.2 to 3.0 wt. % chlorine or fluorine. Other catalytic composites may also be used in the reaction zone.

The preferred embodiment of the invention may be characterized as a process for the isomerization of $C_7$-$C_9$ alkylaromatic hydrocarbons which comprises the steps of admixing a feed stream comprising a liquid-phase alkylaromatic hydrocarbon with a recycle gas stream comprising hydrogen and thereby forming a mixed-phase first process stream; vaporizing the liquid-phase portion of the first process stream and also heating the first process stream to the desired isomerization conditions by indirect heat exchange against a vapor-phase second process stream; passing the first process stream through an isomerization zone containing an isomerization catalyst and maintained at isomerization conditions and thereby forming an isomerization zone effluent stream; heating the isomerization zone effluent stream in a fired heater; and cooling the isomerization zone effluent stream by indirect heat exchange against the first process stream as the second process stream.

In another embodiment of the invention, an acyclic hydrocarbon such as a normal paraffin having more than four carbon atoms and preferably from five to seven carbon atoms per molecule is isomerized in the reaction zone. This process is described in U.S. Pat. Nos. 2,938,936; 3,112,351; 3,128,319; 3,131,235; 3,283,301 and 3,755,144. It is performed for such purposes as the upgrading of the paraffins to suitable motor fuel blending components, the production of isoparaffins for use in an alkylation process and as part of a combined isomerization-dehydrogenation process for the production of isoolefins.

The preferred paraffin isomerization catalyst composition comprises an alumina-platinum composite which has had chemically combined hydroxyl groups on its surface reacted with alumina chloride or another Friedel-Crafts type halide after the composite has been calcined. It may be exemplified by the catalysts disclosed by U.S. Pat. Nos. 2,999,074 and 3,649,704. The alumina-platinum composite may be prepared by any suitable method, such as coprecipitation or impregnation, and then mildly calcined at about 350° C. to about 700° C., and preferably from 500° C. to 600° C. to remove adsorbed water but still retain hydroxyl groups on the catalyst surface prior to reaction with the halide. The isomerization catalyst may alo comprise other metals such as germanium or rhenium in addition to the platinum.

In general, satisfactory paraffin isomerization catalysts comprise refractory inorganic oxides and a platinum group metal. The solid refractory oxide may be selected from silica, alumina, titanium dioxide, chromia, or mixtures of these oxides; various naturally occurring refractory oxides in differing degrees of purity, such as bauxite and bentonite clay; or diatomaceous earth such as kieselguhr. Of the above mentioned oxides, alumina is preferred, and particularly preferred is synthetically prepared substantially anhydrous gamma alumina with a high degree of purity. By a platinum group metal is meant a noble metal, exclusing silver and gold, selected from the group consisting of platinum, palladium, germanium, ruthenium, rhodium, osmium and iridium. These metals are not necessarily equivalent in activity in the catalyst and of these metals, platinum and palladium are preferred. Recent findings indicate that in some applications other metals, particularly rhenium and germanium, may have a beneficial effect and increase or lengthen catalyst activities. Also normally present in these catalysts is a halogen, termed in the art a combined halogen, and which may be present in an amount of from 0.01 to about 5.0% by weight based on the dried support material, and which is preferably selected from fluorine and chlorine, with chlorine being particularly preferred.

The conditions necessary for successful operation of the reaction zone during isomerization are dependent on both the change material and the specific catalyst used in the reaction zone. For the specific embodiment of isomerization of $C_5$ and $C_6$ normal paraffins, the inlet temperature to the reaction zone may range from 120° C. to about 205° C. and a more particularly preferred operating range would be from 150° C. to 175° C. The isomerization reaction is exothermic and a temperature rise of 18 to 35 Centigrade degrees is normal depending on the degree of conversion and the amount of benzene contained in the charge material. Benzene, which may be present due to poor fractionation of the charge material, exerts a large effect on the reaction zone outlet temperature because the hydrogenation reaction of benzene is more exothermic than the isomerization reaction of the normal paraffin. The reaction zone may be maintained at almost any pressure, but normally the pressure used will be from about 400 psig to about 1500 psig with a preferred range being from 800 psig to 1200 psig and a particularly preferred operating pressure being about 1000 psig.

The process of the subject invention may be used for the isomerization of any type of isomerizable hydrocarbon. The hydrocarbon present in the feed stream may therefore be saturated or unsaturated and may be cyclic or acyclic. For the isomerization of olefinic hydrocarbons, the reaction zone is preferably operated at a temperature between about 45° C. and about 250° C., with a temperature between about 75° C. and 160° C. being especially preferred. The pressure maintained within the reaction zone may range from superatmospheric to about 30 atmospheres. The preferred olefin isomerization catalyst is one which comprises sulfided nickel supported on a refractory inorganic base similar to the isomerization catalyst described in U.S. Pat. No. 3,821,133. The feed stream to the reaction zone will preferably contain from 0.1 to 1.0 mole of hydrogen per mole of hydrocarbon. An olefin liquid hourly space velocity (liquid volume of feed olefin per hour per unit volume of catalyst employed) of between 0.5 and 20 may be employed, with olefin liquid hourly space velocities of between 1.0 and 10.0 being preferred. An acyclic olefinic hydrocarbon processed according to the subject invention preferably has between four and ten carbon atoms per molecule.

I claim as my invention:

1. A hydrocarbon isomerization process which comprises the steps of:
   (a) vaporizing the liquid phase portion of a mixed-phase isomerization zone feed stream which comprises a $C_5$–$C_{12}$ hydrocarbon and also heating the isomerization zone feed stream to an isomerization temperature by indirect heat exchange against a vapor-phase process stream;
   (b) passing the isomerization zone feed stream into a hydrocarbon isomerization zone containing an isomerization catalyst and maintained at isomerization conditions and thereby forming a vapor-phase isomerization zone effluent stream which comprises two different hydrocarbons;
   (c) heating at least a portion of the isomerization zone effluent stream in a fired heater; and,
   (d) cooling the heated portion of the isomerization zone effluent stream by indirect heat exchange against the feed stream as the vapor-phase process stream of step (a).

2. The process of claim 1 further characterized in that the $C_5$–$C_{12}$ hydrocarbon of the feed stream is a saturated acyclic hydrocarbon.

3. The process of claim 1 further characterized in that the $C_5$–$C_{12}$ hydrocarbon of the feed stream is an unsaturated cyclic hydrocarbon.

4. A process for the isomerization of acyclic hydrocarbons which comprises the steps of:
   (a) admixing the feed stream comprising a liquid-phase $C_5$-plus acyclic hydrocarbon with a recycle gas stream comprising hydrogen and thereby forming a mixed-phase first process stream;
   (b) vaporizing the liquid-phase portion of the first process stream and also heating the first process stream to isomerization temperature by indirect heat exchange against a vapor-phase second process stream;
   (c) passing the first process stream through an isomerization zone containing an isomerization catalyst and maintained at isomerization conditions and thereby forming an isomerization zone effluent stream;
   (d) heating the isomerization zone effluent stream in a fired heater; and,
   (e) cooling the isomerization zone effluent stream by indirect heat exchange against the first process stream as the second process stream.

5. The process of claim 4 further characterized in that the feed stream comprises a $C_6$–$C_9$ acyclic hydrocarbon.

6. A process for the isomerization of alkylaromatic hydrocarbons which comprises the steps of:
   (a) admixing a feed stream comprising a liquid-phase alkylaromatic hydrocarbon with a recycle gas stream comprising hydrogen and thereby forming a mixed-phase first process stream;
   (b) vaporizing the liquid-phase portion of the first process stream and also heating the first process stream to the desired isomerization conditions by indirect heat exchange against a vapor-phase second process stream;
   (c) passing the first process stream through an isomerization zone containing an isomerization catalyst and maintained at isomerization conditions and thereby forming an isomerization zone effluent stream;
   (d) heating the isomerization zone effluent stream in a fired heater; and,
   (e) cooling the isomerization zone effluent stream by indirect heat exchange against the first process stream as the second process stream.

7. The process of claim 6 further characterized in that the feed stream comprises a $C_7$–$C_9$ alkylaromatic hydrocarbon.

* * * * *